(12) United States Patent
Christopherson et al.

(10) Patent No.: US 10,932,682 B2
(45) Date of Patent: Mar. 2, 2021

(54) METHOD AND APPARATUS FOR SENSING RESPIRATORY PRESSURE IN AN IMPLANTABLE STIMULATION SYSTEM

(71) Applicant: INSPIRE MEDICAL SYSTEMS, INC., Maple Grove, MN (US)

(72) Inventors: Mark Christopherson, Maple Grove, MN (US); Timothy Herbert, Maple Grove, MN (US); Quan Ni, Maple Grove, MN (US)

(73) Assignee: Inspire Medical Systems, Inc., Golden Valley, MN (US)

( * ) Notice: Subject to any disclaimer, the term of this patent is extended or adjusted under 35 U.S.C. 154(b) by 221 days.

(21) Appl. No.: 15/689,275

(22) Filed: Aug. 29, 2017

(65) Prior Publication Data

US 2018/0103860 A1    Apr. 19, 2018

Related U.S. Application Data (63) Continuation of application No. 12/992,511, filed as application No. PCT/US2009/004427 on May 15, 2009, now abandoned.

(60) Provisional application No. 61/053,344, filed on May 15, 2008.

(51) Int. Cl.
*A61B 5/03* (2006.01)
*A61B 5/01* (2006.01)
*A61B 5/00* (2006.01)
*A61N 1/36* (2006.01)
*A61N 1/365* (2006.01)

(52) U.S. Cl.
CPC .............. *A61B 5/03* (2013.01); *A61B 5/01* (2013.01); *A61B 5/4818* (2013.01); *A61N 1/3601* (2013.01); *A61N 1/36514* (2013.01); *A61N 1/36521* (2013.01)

(58) Field of Classification Search
CPC .. A61N 1/3601; A61B 5/4818; A61B 5/0031; A61B 5/03
See application file for complete search history.

(56) References Cited

U.S. PATENT DOCUMENTS

| | | | |
|---|---|---|---|
| 4,567,892 | A | 2/1986 | Plicchi et al. |
| 4,813,431 | A | 3/1989 | Brown |
| 5,098,442 | A | 3/1992 | Grandjean |
| 5,107,856 | A | 4/1992 | Kristiansen et al. |
| 5,158,080 | A | 10/1992 | Kallock |
| 5,344,438 | A | 9/1994 | Testerman |

(Continued)

FOREIGN PATENT DOCUMENTS

| | | |
|---|---|---|
| JP | H09-215757 | 8/1997 |
| JP | H10-248941 | 9/1998 |

(Continued)

OTHER PUBLICATIONS

EP Communication, Extended European Search Report, dated Apr. 17, 2018, 12 pages.

(Continued)

*Primary Examiner* — Jacqueline Cheng
*Assistant Examiner* — Michael A Catina
(74) *Attorney, Agent, or Firm* — Dicke, Billig & Czaja, PLLC (57) ABSTRACT

A method and system for sensing respiration in the treatment of sleep apnea is disclosed.

14 Claims, 9 Drawing Sheets

(56) References Cited

U.S. PATENT DOCUMENTS

| | | | |
|---|---|---|---|
| 5,353,800 A | 10/1994 | Pohndorf et al. | |
| 5,423,763 A | 6/1995 | Helland et al. | |
| 5,485,851 A | 1/1996 | Erickson | |
| 5,540,731 A | 7/1996 | Testerman | |
| 5,540,732 A | 7/1996 | Testerman | |
| 5,540,733 A | 7/1996 | Testerman | |
| 5,546,952 A | 9/1996 | Erickson | |
| 5,876,429 A | 3/1999 | Schroeppel | |
| 5,860,938 A | 4/1999 | Christopherson et al. | |
| 5,895,360 A | 4/1999 | Christopherson et al. | |
| 5,916,221 A | 7/1999 | Miesel | |
| 5,919,221 A | 7/1999 | Miesel | |
| 5,944,680 A | 8/1999 | Christopherson et al. | |
| 6,015,389 A | 1/2000 | Brown | |
| 6,099,479 A | 8/2000 | Christopherson et al. | |
| 6,132,384 A * | 10/2000 | Christopherson | A61B 5/03 |
| | | | 600/529 |
| 6,309,350 B1 | 10/2001 | Van Tassel et al. | |
| 6,572,543 B1 | 6/2003 | Christopherson et al. | |
| 6,647,289 B2 | 11/2003 | Prutchi | |
| 6,651,652 B1 | 11/2003 | Ward | |
| 6,712,772 B2 | 3/2004 | Cohen et al. | |
| 6,770,070 B1 | 8/2004 | Balbierz | |
| 7,054,692 B1 | 5/2006 | Whitehurst et al. | |
| 7,065,410 B2 | 6/2006 | Bardy et al. | |
| 7,066,031 B2 | 6/2006 | Zdeblick et al. | |
| 7,128,717 B1 | 10/2006 | Thach et al. | |
| 7,160,255 B2 | 1/2007 | Saadat | |
| 7,167,743 B2 | 1/2007 | Heruth et al. | |
| 7,186,220 B2 | 3/2007 | Stahmann et al. | |
| 7,189,204 B2 | 3/2007 | Ni et al. | |
| 7,200,440 B2 | 4/2007 | Kim et al. | |
| 7,252,640 B2 | 8/2007 | Ni et al. | |
| 7,330,760 B2 | 2/2008 | Heruth et al. | |
| 7,336,996 B2 | 2/2008 | Hartley et al. | |
| 7,395,113 B2 | 7/2008 | Heruth et al. | |
| 7,396,333 B2 | 7/2008 | Stahmann et al. | |
| 7,447,545 B2 | 11/2008 | Heruth et al. | |
| 7,468,040 B2 | 12/2008 | Hartley et al. | |
| 7,469,697 B2 | 12/2008 | Lee et al. | |
| 7,477,323 B2 | 1/2009 | Chou | |
| 7,491,181 B2 | 2/2009 | Heruth et al. | |
| 7,510,531 B2 | 3/2009 | Lee et al. | |
| 7,542,803 B2 | 6/2009 | Heruth et al. | |
| 7,572,225 B2 | 8/2009 | Stahmann et al. | |
| 7,575,690 B2 | 8/2009 | Mesher et al. | |
| 7,590,455 B2 | 9/2009 | Heruth et al. | |
| 7,591,265 B2 | 9/2009 | Lee et al. | |
| 7,634,315 B2 | 12/2009 | Cholette | |
| 7,644,714 B2 | 1/2010 | Atkinson et al. | |
| 7,678,061 B2 | 3/2010 | Lee et al. | |
| 7,717,848 B2 | 5/2010 | Heruth et al. | |
| 7,720,541 B2 | 5/2010 | Stahmann et al. | |
| 7,725,195 B2 | 5/2010 | Lima et al. | |
| 7,726,209 B2 | 6/2010 | Ruotoistenmaki | |
| 7,775,993 B2 | 8/2010 | Heruth et al. | |
| 7,783,353 B2 | 8/2010 | Libbus et al. | |
| 7,792,583 B2 | 9/2010 | Miesel et al. | |
| 7,809,442 B2 | 10/2010 | Bolea et al. | |
| 7,853,322 B2 | 12/2010 | Bourget et al. | |
| 7,881,798 B2 | 2/2011 | Miesel et al. | |
| 7,908,013 B2 | 3/2011 | Miesel et al. | |
| 7,957,797 B2 | 6/2011 | Bourget et al. | |
| 7,957,809 B2 | 6/2011 | Bourget et al. | |
| 7,979,128 B2 | 7/2011 | Tehrani et al. | |
| 8,016,776 B2 | 9/2011 | Bourget et al. | |
| 8,021,299 B2 | 9/2011 | Miesel et al. | |
| 8,050,531 B2 | 11/2011 | Rahman et al. | |
| 8,160,711 B2 | 4/2012 | Tehrani et al. | |
| 8,175,720 B2 | 5/2012 | Skelton et al. | |
| 8,489,189 B2 | 7/2013 | Tronnes | |
| 2001/0010010 A1 | 7/2001 | Richmond et al. | |
| 2002/0010495 A1 | 1/2002 | Freed et al. | |
| 2003/0093128 A1 | 5/2003 | Freed et al. | |
| 2003/0163059 A1 | 8/2003 | Poezevera et al. | |
| 2004/0116819 A1 | 6/2004 | Alt | |
| 2004/0162499 A1 | 8/2004 | Nagai et al. | |
| 2005/0004610 A1 | 1/2005 | Kim et al. | |
| 2005/0042589 A1 | 2/2005 | Hatlestad et al. | |
| 2005/0043772 A1 | 2/2005 | Stahmann et al. | |
| 2005/0074741 A1 * | 4/2005 | Lee | A61B 5/0031 |
| | | | 434/433 |
| 2005/0076908 A1 | 4/2005 | Lee et al. | |
| 2005/0085865 A1 | 4/2005 | Tehrani | |
| 2005/0085866 A1 | 4/2005 | Tehrani | |
| 2005/0085868 A1 | 4/2005 | Tehrani et al. | |
| 2005/0085869 A1 | 4/2005 | Tehrani et al. | |
| 2005/0101833 A1 | 5/2005 | Hsu et al. | |
| 2005/0115561 A1 | 6/2005 | Stahmann et al. | |
| 2005/0165457 A1 | 7/2005 | Benser et al. | |
| 2005/0261747 A1 | 11/2005 | Schuler et al. | |
| 2005/0267380 A1 | 12/2005 | Poezevara | |
| 2006/0103407 A1 | 5/2006 | Kakizawa et al. | |
| 2006/0142815 A1 | 6/2006 | Tehrani et al. | |
| 2006/0195144 A1 | 8/2006 | Giftakis et al. | |
| 2006/0259079 A1 | 11/2006 | King | |
| 2006/0276701 A1 | 12/2006 | Ray | |
| 2006/0282127 A1 | 12/2006 | Zealear | |
| 2007/0233204 A1 | 10/2007 | Lima et al. | |
| 2008/0103545 A1 * | 5/2008 | Bolea | A61N 1/0556 |
| | | | 607/42 |
| 2008/0161877 A1 | 7/2008 | Kirby et al. | |
| 2009/0112116 A1 | 9/2009 | Lee et al. | |
| 2009/0266369 A1 | 10/2009 | Johnson et al. | |
| 2009/0270707 A1 | 10/2009 | Alfoqaha et al. | |
| 2009/0308395 A1 | 12/2009 | Lee et al. | |
| 2010/0094379 A1 | 4/2010 | Meadows et al. | |
| 2010/0137931 A1 | 6/2010 | Hopper et al. | |
| 2010/0174341 A1 | 7/2010 | Bolea et al. | |
| 2010/0198103 A1 | 8/2010 | Meadows et al. | |
| 2010/0241195 A1 | 9/2010 | Meadows et al. | |
| 2011/0093036 A1 | 4/2011 | Mashiach | |
| 2011/0152965 A1 | 6/2011 | Mashiach et al. | |

FOREIGN PATENT DOCUMENTS

| | | |
|---|---|---|
| WO | 2006102591 | 9/2006 |
| WO | 200711486 | 10/2007 |
| WO | 2009048580 | 4/2009 |
| WO | 2009048581 | 4/2009 |
| WO | 2009135138 | 11/2009 |
| WO | 2009135140 | 11/2009 |
| WO | 2009135142 | 11/2009 |
| WO | 2009140636 | 11/2009 |
| WO | 2010039853 | 4/2010 |
| WO | 2010059839 | 5/2010 |
| WO | 2010117810 | 10/2010 |

OTHER PUBLICATIONS

Eisele Article—David W. Eisele, MD et al., "Tongue neuromuscular and direct hypoglossal nerve stimulation for obstructive sleep apnea," Otolaryngologic Clinics of North America, Otolayngol Clin N Am 36 (2003) 501-510 (10 pages).

Oliven Article—Arie Oliven et al., "Upper airway response to electrical stimulation of the genioglossus in obstructive sleep apnea," Journal of Applied Physiology, vol. 95, pp. 2023-2029, Nov. 2003, www.jap.physiology.org on Sep. 18, 2006. (8 pages).

Schwartz Article—Alan R. Schwartz MD et al., Theraputic Electrical Stimulation of the Hypoglossal Nerve in Obstructive Sleep Apnea, Arch Otolaryngol Head And Neck Surg., vol. 127, Oct. 2001, pp. 1216-1223. Copyright 2001 American Medical Association. (8 pages).

Park Article—Jung I. Park MD, PhD, "Preoperative Percutaneous Cranial Nerve Mapping in Head and Neck Surgery", American Medical Association, 2003, (6 pages).

* cited by examiner

METHOD AND APPARATUS FOR SENSING RESPIRATORY PRESSURE IN AN IMPLANTABLE STIMULATION SYSTEM

CROSS-REFERENCE TO RELATED APPLICATIONS

This application is a Continuation of U.S. application Ser. No. 12/992,511, which entered National Stage Mar. 7, 2011, based on PCT/US2009/04427, filed May 15, 2009, which claimed priority to U.S. Provisional Patent Application Ser. No. 61/053,344, filed May 15, 2008, all of which are incorporated herein by reference.

TECHNICAL FIELD

The invention relates generally to an implantable stimulation system for stimulating and monitoring soft tissue in a patient, and more particularly, the invention relates to a method and apparatus for sensing respiratory pressure to control delivery of therapy to nerve tissue.

BACKGROUND

Sleep apnea generally refers to the cessation of breathing during sleep. One type of sleep apnea, referred to as obstructive sleep apnea (OSA), is characterized by repetitive pauses in breathing during sleep due to the obstruction and/or collapse of the upper airway, and is usually accompanied by a reduction in blood oxygenation saturation.

One treatment for obstructive sleep apnea has included the delivery of electrical stimulation to the hypoglossal nerve, located in the neck region under the chin. Such stimulation therapy activates the upper airway muscles to maintain upper airway patency. In treatment of sleep apnea, increased respiratory effort resulting from the difficulty in breathing through an obstructed airway is avoided by synchronized stimulation of an upper airway muscle or muscle group that holds the airway open during the inspiratory phase of breathing. For example, the genioglossus muscle is stimulated during treatment of sleep apnea by a cuff electrode place around the hypoglossal nerve.

In addition to positioning an electrode to deliver the therapy to the nerve, obstructive sleep apnea treatment may include the use of a sensor that is surgically implanted in a region that has pressure continuity with the intrapleural space, such as the suprasternal notch, the space between the trachea and esophagus, or by being attached to either of the trachea or esophagus. The sensor may also be positioned intercostally, or secured in a position for sensing pressure at the posterior side of the manubrium. The suprasternal notch and manubrium of the sternum are well known structures on the upper chest that are in anatomical continuity with the intrapleural space. Changes in intrapleural pressure provide a characteristic respiratory effort waveform, and therefore the sensor enables respiratory effort waveform information to be utilized to determine increased respiratory effort, which is then used to control delivery of therapy in response to determined increases in respiratory effort.

The location for placement of the sensor is, at least in part, chosen as a function of a delay, i.e. the propagation time associated with a pressure waveform characteristic of respiratory effort propagating from the respiratory point of origin to the sensor position. The chosen location is also a function of the amount of filtering necessary to achieve a usable sensed signal at a particular location, i.e. the amount of filtering that is used to remove waveforms other than the waveform associated with the desired sensed characteristic, such as the filtering required to remove cardiac waveform activity, for example.

However, in some conventional locations for sensor placement, the sensed signal tends to be corrupted by an added signal artifacts caused by cardiac vessels because of the close proximity of cardiac vessels to the sensor. In addition, implanting the sensor using the known placement positions tends to be an invasive procedure.

Accordingly, significant challenges remain in providing effective respiratory sensing in the treatment of sleep apnea.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts. Accordingly, aspects and features of the present disclosure will be appreciated as the same becomes better understood by reference to the following detailed description of the embodiments when considered in connection with the accompanying drawings, wherein.

DETAILED DESCRIPTION OF EMBODIMENTS

The following detailed description is merely exemplary in nature and is not intended to limit the present disclosure or the application and uses of the embodiments of the present disclosure. Furthermore, there is no intention to be bound by any expressed or implied theory presented in the preceding technical field, background, brief summary or the following detailed description.

Accordingly, in the following Detailed Description, reference is made to the accompanying drawings, which form a part hereof, and in which is shown by way of illustration specific embodiments in which the present invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present disclosure. The following detailed description, therefore, is not to be taken in a limiting sense, and the scope of the present invention is defined by the appended claims.

Figure 1:
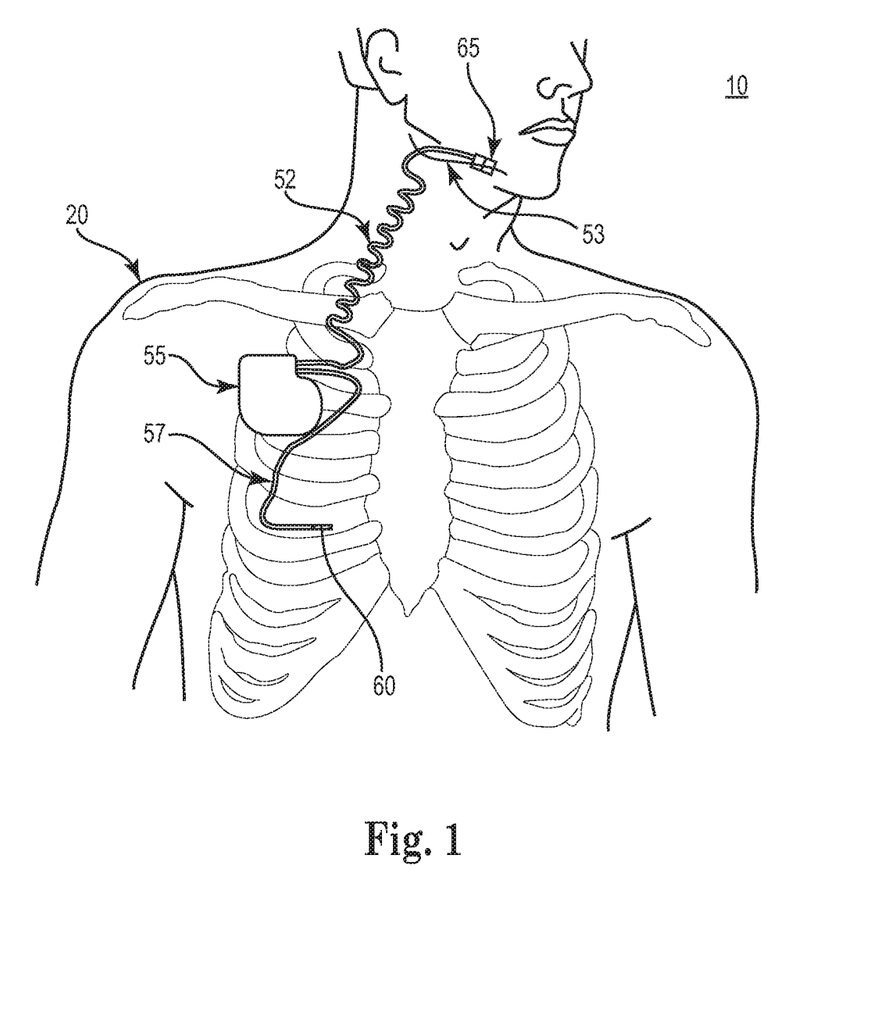
FIG. 1 is a front view schematically illustrating an implantable stimulation system deployed in a patient, according to one embodiment of the present disclosure.

FIG. 1 is a schematic diagram of an implantable stimulation system, according to an embodiment of the present disclosure. As illustrated in FIG. 1, an example of an implantable stimulation system 10 according to one embodiment of the present disclosure includes an implantable pulse generator (IPG) 55, capable of being surgically positioned within a pectoral region of a patient 20, and a stimulation lead 52 electrically coupled with the IPG 55 via a connector (not shown) positioned within a connection port of the IPG 55. The lead 52 includes an electrode or electrode system 65 and extends from the IPG 55 so that the electrode system 65 is positioned in proximity to a desired nerve, such as the hypoglossal nerve 53 of the patient 20, to enable stimulation of the nerve 53, as described below in detail. In one embodiment, an implantable stimulation system in which lead 52 may be utilized, for example, is described in U.S. Pat. No. 6,572,543 to Christopherson et al., which is incorporated herein by reference in its entirety. In this exemplary system, a sensor lead 57 is electrically coupled to the IPG 55 and extends from the IPG 55 so that a sensor or transducer 60 can be positioned in the patient 20 for sensing of respiratory effort. However, it is understood that respiratory sensing embodiments described herein can be used with other implantable stimulation systems for treating sleep apnea.

In some embodiments, system 10 also comprises additional sensors to obtain further physiologic data associated with respiratory functions, such as various sensors distributed about the chest area for measuring a trans-thoracic bio-impedance signal, an electrocardiogram (ECG) signal, or other respiratory-associated signals.

In some embodiments, the sensing and stimulation system for treating obstructive sleep apnea is a totally implantable system which provides therapeutic solutions for patients diagnosed with obstructive sleep apnea. In other embodiments, one or more components of the system are not implanted in a body of the patient. A few non-limiting examples of such non-implanted components include external sensors (e.g., impedance, heart rate, etc.), an external processing unit, or an external power source. Of course, it is further understood that the implanted portion(s) of the system provides a communication pathway to enable transmission of data and/or controls signals both to and from the implanted portions of the system relative to the external portions of the system. The communication pathway includes a radiofrequency (RF) telemetry link or other wireless communication protocols.

Whether partially implantable or totally implantable, the system is designed to stimulate the hypoglossal nerve during inspiration to thereby prevent obstructions or occlusions in the upper airway during sleep. In one embodiment, the implantable system comprises an implantable pulse generator (IPG), a peripheral nerve cuff stimulation lead, and a respiratory sensing lead.

Figure 2:
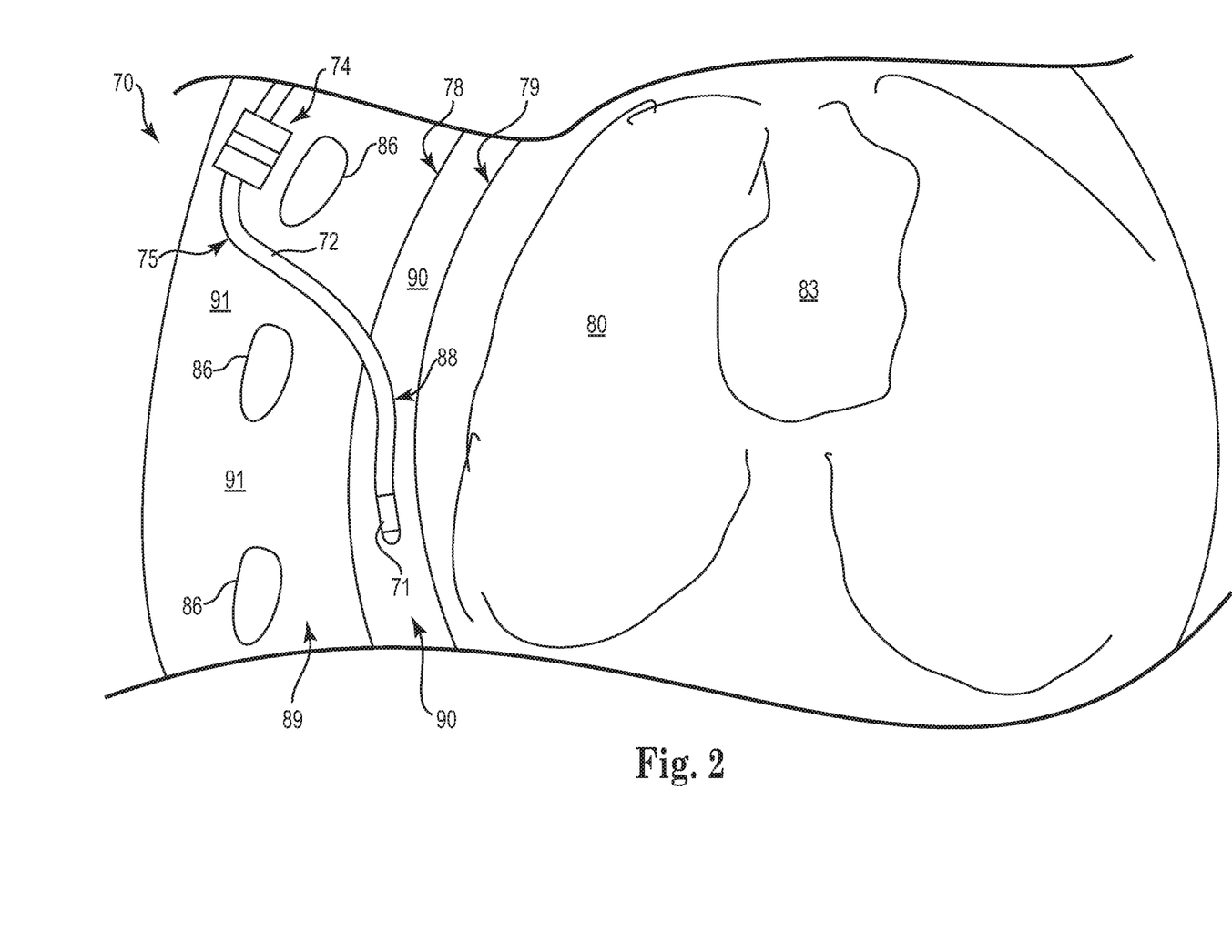
FIG. 2 is a schematic illustration of a sensor lead deployed intrapleurally, according to one embodiment of the present disclosure.

In one embodiment, the sensor 60 is a respiratory pressure sensor that is surgically implanted in a region that has pressure continuity with the pleura via an intrapleural placement or an extrapleural placement (including but not limited to an intercostal placement), as will be further described in association with FIG. 2. The location for placement of the sensor 60 is, at least in part, chosen as a function of a delay, i.e. the propagation time associated with a pressure waveform characteristic of respiratory effort propagating from the respiratory point of origin to the sensor position. The chosen location is also a function of the amount of filtering or signal processing necessary to achieve a usable sensed signal at a particular location, i.e. the amount of filtering that is necessary to remove waveforms other than the waveform associated with the desired sensed characteristic, such as the filtering required to remove cardiac waveform activity, for example. The positioning of the sensor 60 enables the IPG 55 to receive respiratory effort waveform information and to use this information to control delivery of the therapy.

As schematically illustrated in FIG. 2, in one embodiment of the present disclosure, an implantable stimulation system 10 comprises a sensing system 70 including a lead 75 configured to place a respiratory pressure sensor 71 within an intrapleural space 90 so that sensor 71 is positioned in close proximity to the lung 80. In this arrangement, the sensor 71 becomes directly coupled relative to the respiratory pressures at the pleura. In another aspect, the intrapleural space 90 includes the cavity between the parietal pleura 78 and a pulmonary pleura 79. Finally, it will be understood that FIG. 2 illustrates generous spacing between adjacent anatomical structures for illustrative purposes.

In the one embodiment, lead 75 includes a lead body 72 that supports sensor 71 at its distal end and an anchor 74 (such as a wing-like fixation member) located at a more proximal portion of lead body 72. The anchor 74 ensures that sensor 71 remains positioned to orient the membrane portion of the sensor to face along the lung 80 subsequent to implantation of the sensor 71. The lead body 72 is positioned through an inter-costal space 91 into the pleural space 90 (with a position of sensor 71 and lead body 72 as indicated by reference numeral 88) so that the IPG 55 (FIG. 1) receives sensor waveforms from the sensor 71, thereby enabling the IPG 55 (FIG. 1) to deliver electrical stimulation synchronously with inspiration, according to a therapeutic treatment regimen in accordance with embodiments of the present disclosure.

As further illustrated by FIG. 2, the lead 75 will be inserted so that lead body 72 extends through the intercostal space (e.g. between two ribs 86) to position the sensor 71 for placement intrapleurally, as indicated generally via indicator 90. In one embodiment, the lead 75 incorporates a piezo-electric crystal mounted into a sealed housing and capable of monitoring intra-thoracic pressure associated with respiration. In other embodiments, monitoring the respiratory pressure comprises monitoring other physiological data indicative of respiratory pressure (in addition to or instead of monitoring intra-thoracic pressure). The sensor 71 is powered by the IPG 55 (FIG. 1) and the IPG 55 also contains internal circuitry to accept and process the respiration signal from the lead 75.

In one embodiment, the system includes a lead anchor 74 located remotely (by a distance of several centimeters or so) from where the sensor 71 is placed intrapleurally. Tissue movements on the sensor and lead can induce unwanted signal components as well as lead migration/dislodgement; therefore anchoring of the lead body 72, close to where the lead 75 enters the thoracic cavity is warranted. With this in mind, the anchor 74 will be sutured to a subcutaneous connective tissue, such as an intra-costal muscle or fascia during implant, and the anchor 74 is fixed or secured to the lead body 72 and not allowed to slide.

In other embodiments, the respiratory sensor can be any one of an airflow sensor, a pressure sensor, a volume sensor, an accelerometer, an acoustic sensor, a temperature sensor, a mechanical strain sensor, or an effort sensor.

Figure 3:
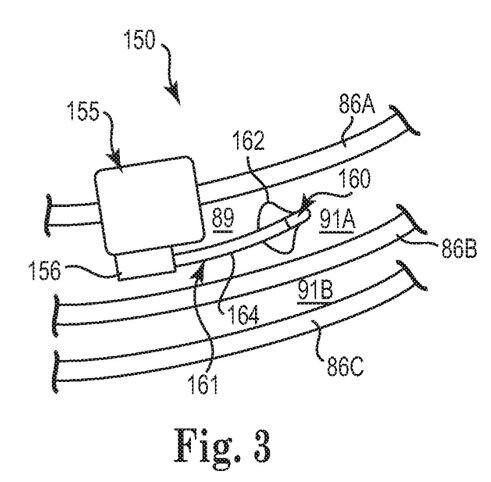
FIG. 3 is a front view schematically illustrating an implantable stimulation system, with a subcutaneous, extrapleural placement, as deployed in a patient, according to one embodiment of the present disclosure.
Figure 4:
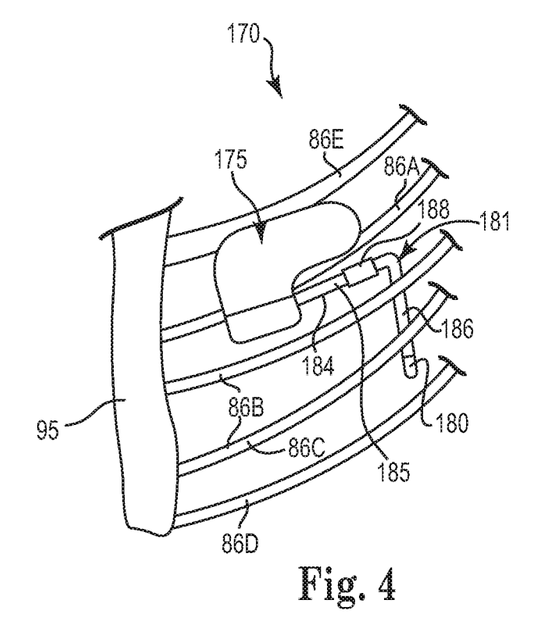
FIG. 4 is a front view schematically illustrating an implantable stimulation system, with an intrapleural placement, as deployed in a patient, according to another embodiment of the present disclosure.

To achieve the placement of the sensor 60 in the positions shown and described in association with FIGS. 1-2, several different approaches can be taken as illustrated in association with at least FIGS. 3-4.

FIG. 3 schematically illustrates an implantable stimulation system 150, with a subcutaneous, extrapleural placement, according to one embodiment of the present disclosure. As shown in FIG. 3, system 150 includes an IPG 155 and a sensor lead 161. In one embodiment, the IPG 155 includes at least substantially the same features and attributes as IPG 55 (FIG. 1).

In general terms, the sensor lead 161 is configured to detect and/or measure respiratory effort in a manner substantially similar to the sensor 60, as previously described in association with FIGS. 1-2, except for having a generally shorter length for sensor lead 161. With this in mind, as shown in FIG. 3, sensor lead 161 includes sensor portion 160, lead body 164, and stability mechanism 162. In one aspect, lead body 164 has a relatively short length such that with the IPG 155 mounted generally over one or more ribs (e.g. such as ribs 86A, 86B, etc.), lead body 164 forms a generally straight portion extending directly from the header 156 of IPG 155 to cause lead body 164 to extend generally parallel to ribs 86A, 86B. It will be understood that, in some embodiments, lead body 164 will have a length greater than that shown in FIG. 3.

As illustrated in FIG. 3, sensor lead 161 is implanted in a subcutaneous, extrapleural region 89 (which also includes but is not limited to placement intercostally between a pair of spaced apart ribs 86) that is external to the parietal pleura 78 (FIG. 2). In this subcutaneous, extrapleural position 89 the sensor portion 160 can be against the parietal pleura 78 or within the tissues (which includes several layers of the muscle and related connective tissues) that are external to the parietal pleura 78 and which are accessible between an adjacent pair of ribs. In one aspect, in this arrangement the sensor portion 160 becomes indirectly coupled relative to the respiratory pressures which are present at the pleural space 90.

In this arrangement, sensor lead 161 terminates at sensor portion 160 between that same pair of ribs 86A, 86B. In other words, the sensor lead 161 originates from the IPG 155 between adjacent ribs 86A and 86B, and with sensor lead 161 being generally straight, the entire sensor lead 161 remains within this intercostal space 91A between ribs. Accordingly, in this embodiment, sensor lead 161 does not extend across ribs 86A, 86B in either a superior orientation (toward the head) or an inferior orientation (toward the feet) relative to this intercostal space 91B.

In general terms, the stability mechanism 162 of sensor lead 161 ensures that the sensor portion 160 remains generally fixed in a target location so that a membrane portion of the sensor portion 160 is located to be facing along the lung subsequent to implantation of the sensor 160. Being made from a resilient material, the stability mechanism 162 is flexible enough to facilitate its positioning and not interfere with the surrounding tissues, while still having enough stiffness to hold or maintain its position. In this secured position, the sensor portion 160 is located between ribs 86A, 86B in either of an intrapleural or extrapleural implanted configuration (as previously described in association with FIG. 2).

In one embodiment, the stability mechanism 162 includes a pair of wings that extend laterally outward from both sides of the sensor portion 160, as later described in more detail in association with FIGS. 5-6. In some other embodiments, the stability mechanism 162 comprises one or more pairs of anchor elements (e.g. arms) that extend laterally outward from both sides of the sensor lead 161, as later described in more detail in association with at least FIGS. 7-8. In one aspect, these wings or arms of the stability mechanism 162 prevent lateral shifting and/or prevent rotation of the sensor portion 160 to ensure that an active portion of the sensor portion 160 is oriented to face toward the pleura and lungs.

One of the other approaches that achieves an intrapleural placement (consistent with the embodiment of FIG. 2) of a sensor lead is schematically illustrated in association with FIG. 4, according to one embodiment of the present disclosure. As shown in FIG. 4, implantable stimulation system 170 includes an IPG 175 and a sensor lead 181. In one embodiment, the IPG 175 includes at least substantially the same features and attributes as IPG 55 (FIG. 1).

In general terms, the sensor lead 181 is configured to detect and/or measure respiratory effort in a manner substantially similar to the sensor 60, as previously described in association with FIGS. 1-2, except for having a generally shorter length for sensor lead 181. With this in mind, as shown in FIG. 3, sensor lead 181 includes sensor portion 180, lead body 185 (with proximal lead portion 184 and distal lead portion 186), and stability mechanism 188. In one aspect, lead body 185 has a relatively short length such that with the IPG 155 mounted generally over a pair of ribs 86E, 86A, the proximal lead portion 184 forms a generally straight portion extending directly from the header 176 of IPG 155 to cause proximal lead portion 184 to extend between, and generally parallel to, the spaced apart ribs 86A, 86B (which separately connect to manubrium 95 as later described in more detail in association with FIG. 9A).

In one aspect, stability mechanism 188 (e.g., anchor 280 in FIG. 7) is located along the proximal lead portion 184 and secures the proximal lead portion 184 relative to intercostal tissue or adjacent tissues. In another aspect, with proximal lead portion 184 anchored via the stability mechanism 188, distal lead portion 186 forms a generally perpendicular angle relative to the proximal lead portion 184 such that distal lead portion 186 is arranged to extend downward underneath one or more ribs 86D, 86E before terminating at sensor portion 180 within the intrapleural space (as shown in FIG. 2).

In this arrangement, the distal lead portion 186 is oriented to be generally perpendicular to a longitudinal axis of the ribs (or relative to a longitudinal axis of a length of the patient's body) to maintain the sensor portion 180 in a generally vertical orientation within the pleura 90 (FIG. 2). This orientation ensures that normal, cyclical movements of the lungs 80 (FIG. 2) during respiration in a generally vertical orientation (toward and away from the head) do not substantially affect the sensing performed by the sensor portion 180 because a longitudinal axis of the sensor portion 180 is aligned along the direction of movement (and not transverse to) of the lungs.

Nevertheless, it will be understood that in some other embodiments, the sensor portion 180 can be implanted intrapleurally with the distal lead portion 186 extending generally parallel to the longitudinal axis of the ribs to orient the sensor portion 180 in a generally horizontal position within the pleura 90. In these embodiments, portions of the distal lead portion 186 proximal to the sensor portion 180 will be positioned between, and extend generally parallel to, an adjacent pairs of ribs in a manner substantially similar to that shown in FIG. 1 or 3.

Figure 5:
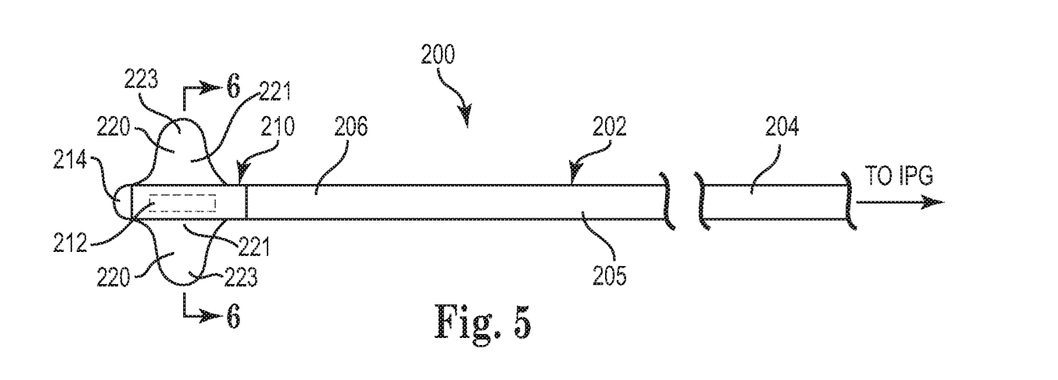
FIG. 5 is a top plan view of a sensor lead, according to one embodiment of the present disclosure.
Figure 6:
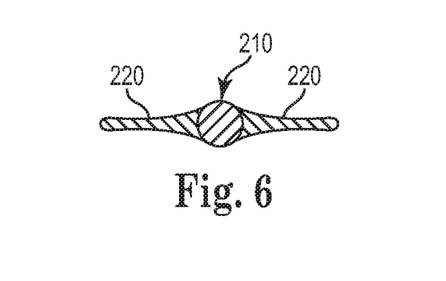
FIG. 6 is a sectional view as taken along lines 6-6 of FIG. 5, according to one embodiment of the present disclosure.

In some embodiments, the stability mechanism 188 of the embodiment of FIG. 4 can be exchanged for the stability mechanism 162 of the embodiment of FIG. 3 (or the stability mechanism provided by wing-like members 220 of FIG. 5), and vice versa.

Among other features, the embodiments of FIGS. 3-4 allow a relatively simple implantation of an IPG and its sensor lead. While an implantation of the IPG and sensor lead on a right side of the patient's body is preferred, in some other embodiments an implantation of the IPG and sensor lead can be made on a left side of the patient's body.

FIG. 5 is a top plan view schematically illustrating a sensor lead 200, according to one embodiment of the present disclosure. In general terms, sensor lead 200 provides a sensor portion 210 including a pair of wing-like members 220 configured to stabilize the position of sensor portion 210 in its implanted location, in manner substantially similar to that previously described in association with at least FIG. 3. As illustrated in FIG. 5, sensor lead 200 comprises a lead body 202 and sensor portion 210. Lead body 202 includes a distal portion 206 supporting sensor portion 210, a midportion 205, and a proximal portion 204 configured to extend to (and connect with) IPG 55 of FIG. 1.

In one aspect, sensor portion 210 includes a distal tip 214, which is preferably made of a soft radiopaque material to be visible under fluoroscopy or other radiograph visualization techniques. In another aspect, sensor portion 210 includes the wing-like members 220, which extend outward from opposite sides of the sensor portion 210. While the wing-like members 220 can take a variety of shapes, the members 220 shown in FIG. 6 have a tapered shape in which each member 220 has a generally wide base 221 and the wing-like members 220 become progressively narrower toward curved tip 223. As further shown in the sectional view of FIG. 6, wing-like members 220 have a generally flat cross-sectional shape. However, in some embodiments, the base 221 is thicker than the tip 223 to ensure robust attachment of the members 220 relative to a body of the sensor portion 220.

In one embodiment, the wing-like members 220 do not include any holes or other features configured to facilitate suturing (or other fastening techniques) of the wing-like members 220 relative to the tissues. Instead, the generally large surface area and resiliency of the wing-like members 220 as they extend outward from the sensor portion 210 provide frictional engagement relative to, and physical abutment to, surrounding tissues. In this way, the wing-like members 220 provide a mechanism that maintains the position of sensor portion 210 in a proper orientation relative to the tissue to be sensed. In particular, in some embodiments, the sensor portion 210 includes a directional sensor element 212 (shown in dashed lines) with sensor portion 210 implanted to cause the directional sensor element 212 face the pleura and target lung tissue. In this arrangement, the wing-like members 220 prevent rotation of the directional sensor element away from the target tissue, while also preventing migration of the sensor portion 210 up, down, left, or right relative its implanted position in the body.

In another aspect, sensor element 212 is configured to perform pressure sensing with sensor element 212 comprising an electronic sensor element that includes one or more piezo-crystal elements, as later described in more detail in association with FIGS. 10-12.

Figure 7:
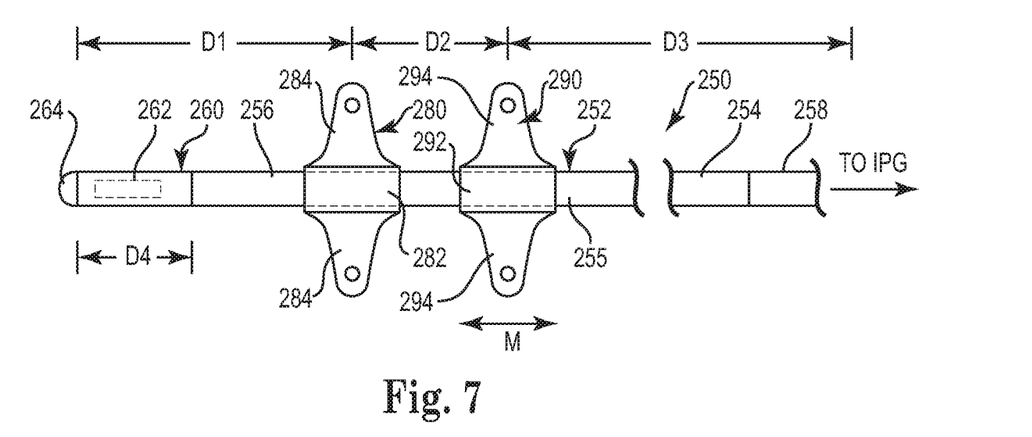
FIG. 7 is a top plan view of a sensor lead, according to one embodiment of the present disclosure.
Figure 8:
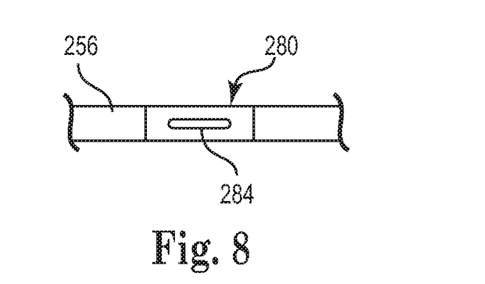
FIG. 8 is a partial side view of an anchor of the sensor lead of FIG. 7, according to one embodiment of the present disclosure.

FIG. 7 is a top plan view schematically illustrating a sensor lead 250, according to one embodiment of the present disclosure. As illustrated in FIG. 7, sensor lead 250 comprises lead body 252 and sensor portion 260. In one embodiment, sensor lead 250 comprises substantially the same features and attributes as sensor 60 as previously described in association with at least FIGS. 1-2. As shown in FIG. 7, sensor portion 260 includes distal tip 264 and sensor element 262. In one aspect, sensor portion 260 has a length (D4) of about 1-3 centimeters.

Lead body 252 includes midportion 255, a proximal portion 254, and a distal portion 256. The distal portion 256 supports sensor portion 260 while the proximal portion 254 configured to extend to, and connect with, IPG 55 (FIG. 1).

In some embodiments, sensor lead 250 includes a first anchor element 280 mounted onto, or formed as part of, lead body 252. In one aspect, first anchor element 280 has a fixed position relative to a length of lead body 252 and includes a pair of arms 284 extending outward from opposite sides of a central portion 282 of anchor element 280. In this position, the arms 284 extend generally perpendicular to a longitudinal axis of the lead body 252. In one embodiment, as illustrated in the side view of FIG. 8, each arm 284 has a thickness substantially less than a diameter of the lead body 252.

In another aspect, each arm 284 includes a hole 285 configured to facilitate suturing (or other fastening techniques) of the arm 284 to surrounding tissues. In some embodiments, the fixed position of first anchor element 280 along lead body 252 is spaced apart a distance (D1) of about 4 to 9 centimeters from the distal tip 264. In other embodiments, the distance (D1) is about 2 to 6 centimeters. In one aspect, this arrangement ensures the sensor lead 250 will extend an adequate distance inside the thoracic cavity or intercostal space to achieve optimal sensing while preventing dislodgements of the sensor lead from its intercostal deployment. Moreover, the resilient arms 284 maintain the orientation of the directional sensor portion 260 to face the lungs or pleura by preventing rotational movement of the sensor portion and/or preventing significant lateral shifting of the sensor portion 260. However, the sensor lead is relatively short enough to avoid interference with cardiac functions, as will be further described in association with FIGS. 9A-9B.

In some embodiments, in addition to fixed first anchor element 280, sensor lead 250 includes a second anchor element 290, as illustrated in FIG. 7. In one aspect, this second anchor element 290 is movable along a length of lead body 252 to enable adjusting the position of the second anchor element 290 before securing it relative to surrounding tissues. In this arrangement, the distance (D2) between the respective anchor elements 280, 290 can vary as desired to effect a robust implantation of sensor lead 250. In one non-limiting use, second anchor element 290 is configured to secure proximal portion 254 of sensor lead 250 after tunneling along a lateral side 303 of the body to and/or from the implanted site of the IPG 55 (FIG. 1).

In one aspect, other than its movable position (as represented by directional arrow M in FIG. 7), second anchor element 290 has substantially the same features and attributes as first anchor element 280. Accordingly, second anchor element 290 has a pair of arms 294 extending outward from opposite sides of central portion 292.

However, it is understood that in other embodiments, the second anchor element 290 can have a fixed position along a length of lead body 252 such that the distance (D2) between the respective anchor elements 280, 290 does not vary.

In some embodiments, lead body 252 includes an outer diameter that is no greater than an outside diameter of the sensor portion 260. Further, in some embodiments, it will be understood that the sensor portion 260 and distal portion 256 of lead body 252 are dip coated with thinned medical adhesive to facilitate maintaining the sensor portion 260 in a desired location relative to the target tissue at which sensing is to take place. At the same time, dip coating also softens the sensor surfaces and provides further electrical insulation.

It will be understood that because the sensor portion 260 will be inserted into the pleural cavity (or adjacent to the pleura, but within the thoracic cavity), the outside diameter of the lead body 252 should be minimized (in concert with the lead body conductor 406 shown in FIG. 11) to optimize the flexibility of the device. This arrangement acts to minimize any local stresses on the sensor portion 260 in the pleural cavity. Likewise, in the situation in which the sensor lead 250 and sensor portion 260 are deployed in an extrapleural configuration, then a relatively small outer diameter of the sensor portion 260 will minimize stress on the pleura.

Figure 9A:
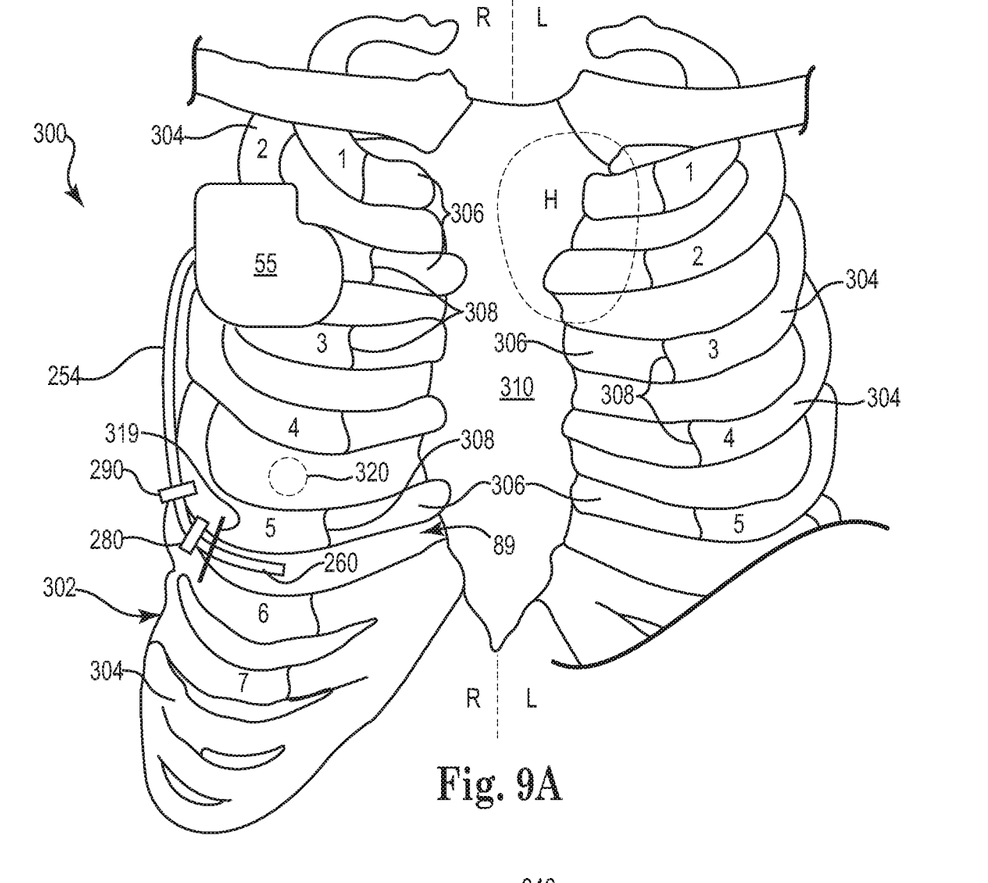
FIG. 9A is a front view schematically illustrating an implantable stimulation system including a respiratory sensor as deployed in a patient, according to one embodiment of the present disclosure.

FIG. 9A is front view schematically illustrating a method 300 of implanting a sensor lead 250 of an implantable stimulation system, according to one embodiment of the present disclosure. As illustrated in FIG. 9A, IPG 55 is implanted in a pectoral region of a patient (FIG. 1) in a manner known to the art such that IPG 55 is positioned over a couple of ribs 304 (such as upper ribs 2 and 3) of a ribcage 302. In some embodiments, the IPG 55 is implanted on a right side (R) of the patient, generally opposite the left side (L) at which the heart H (shown in dashed lines) is located. With further reference to FIG. 9A, a sensor lead 250 extends from the IPG 55 while a stimulation lead (not shown) extends from IPG 55 in a direction opposite the sensor lead 250 for coupling to a target nerve.

As illustrated in FIG. 9A, each rib 304 is joined, via a costochondral joint 308, to a costal cartilage 306. Each costal cartilage 306 is joined to manubrium 310. In one embodiment of method 300, sensor lead 250 is implanted to position sensor portion 260, via intercostal placement, in substantially the same as previously described in association with at least FIGS. 2-4. However, in addition, as shown in method 300, proximal portion 254 of lead body 252 extends down a lateral side 303 of the rib cage 302 (and generally parallel to a longitudinal axis of the body) and distal portion 256 of lead body 252 extends generally parallel to the proximal portion 254. In this arrangement, distal portion 256 and sensor portion 260 extend generally parallel to ribs 304. In one aspect, the point 319 of intercostal entry is selected such that sensor portion 260 will become positioned lateral (toward an outer side of the body) to the costochondral joint 308. In some embodiments, sensor portion 260 is positioned directly below or inferior to the nipple 320. While the nipple is not related functionally to the position of the sensor portion 260, the nipple 320 provides a positional marker relative to a desired location between a lateral side of the body and a midline of the body. In particular, method 300 includes implanting the sensor lead 250 and sensor portion 260 away from the lateral side 303 because that location would compromise the accuracy of the readings from sensor portion 260 when the patient lies on that side of their body to sleep. At the same time, method 300 includes implanting the sensor portion 260 as far away, both laterally and longitudinally, as possible from heart H in order to minimize the effect of cardiac activity on the readings of sensor portion 260. While FIG. 9A shows placement of the sensor portion 260 between the fifth and sixth ribs 304, it will understood that in other embodiments, placement of the sensor portion 260 could take place between any pair of adjacent ribs within the group of ribs 304 extending from the first uppermost rib 304 through the seventh uppermost rib 304.

Moreover, in some embodiments, method 300 also includes implanting the sensor portion 260 over an adequate volume of lung tissue in order to obtain a representative measurement of respiratory effect and activity. This latter constraint practically limits the distance that sensor portion 260 can be located away from heart H because sensor portion 260, in this embodiment, will have to overlie some portion of lung tissue.

Putting all of these constraints together, the sensor lead 250 is implanted to position sensor portion 260 longitudinally between a fifth rib and a sixth rib (over a corresponding portion of lung tissue). At the same time, the sensor portion 260 is positioned lateral (toward a side of the body) of the costochondral joint 208 of either the fifth or sixth rib with the sensor portion 260 also being located directly below or medial to the nipple. However, it is understood that in some other embodiments, the sensor lead 250 and sensor portion 260 can be deployed between a different set of adjacent ribs, such as within the first through seventh rib space, and more preferably within the second through sixth rib space, etc.

Moreover, with this positioning shown in FIG. 9A, first anchor 280 (which is itself fixed relative to lead body 252) is secured in a fixed position at a lateral side 303 of the body within the subcutaneous, extrapleural tissue region 89 that is external to the parietal pleura 78 (FIG. 2) and lateral to the intercostal entry site 319 for the sensor portion 260. In another aspect, the second anchor 290 is located closer toward the IPG 55, and secured to a lateral side 303 of the body as previously described. Because the second anchor 290 is movable, the position of securing the second anchor 290 can be varied to optimize stability of the proximal portion 254 of lead 250 while also supporting the secured position of first anchor 280. Once the desired location of the second anchor 290 is achieved, sutures or other fastening mechanisms are used to fix the second anchor 290 relative to the lead body 252 and relative to subcutaneous connective tissues.

In some embodiments, the deployment location of sensor portion 260 below the nipple 320 (i.e., toward the fee) carries a functional consideration. In particular, by deploying the sensor lead 250 and sensor portion 260 intercostally within the extrapleural region 89 between the fifth and sixth ribs (or between the sixth and seventh ribs), one can avoid penetrating or disturbing the pectoral muscles, and thereby perform the most minimally invasive procedure to place the sensor portion 260 relative to the pleura 90.

Figure 9B:
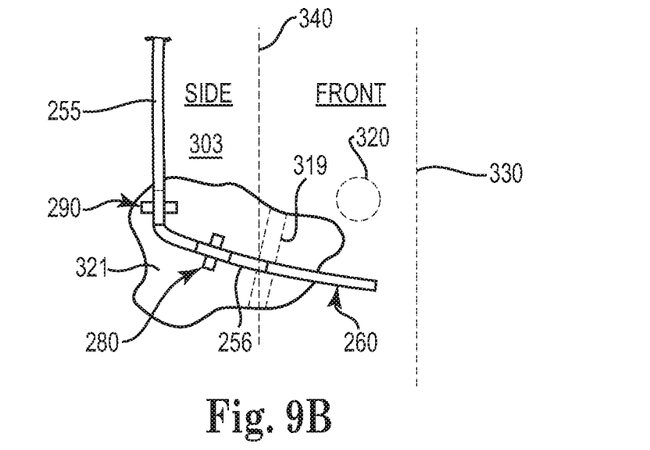
FIG. 9B is a schematic illustration of a method of implanting the sensor lead of FIG. 9A, according to one embodiment of the present disclosure.

FIG. 9B is a diagram that schematically illustrates the position of the sensor lead 250 and sensor portion 260 relative to an incision area 321 and without illustrating the rib cage, as in FIG. 9A. As illustrated in FIG. 9B, the first and second anchors 280, 290 are located on a side portion 303 of the body to cause sensor portion 260 to be positioned lateral (toward outside of body) relative to a costochondral joint (represented by dashed lines 330) of nearby ribs. Moreover, the first anchor 280 is located and secured relative to body tissues external to the intercostal entry site 319 with the distal portion 256 of the lead extending through the intercostal entry site 319 to place the sensor portion 260 within the pleura 90 (see FIG. 2) or in the subcutaneous, extrapleural region 89 between the adjacent ribs (e.g., see FIG. 3 or 9A).

Figure 10:
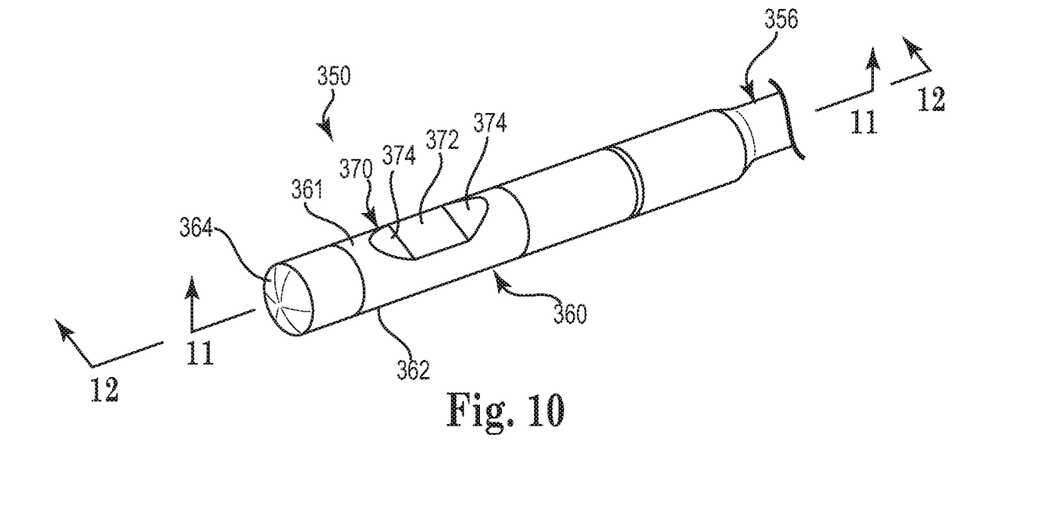
FIG. 10 is a perspective view of a sensor lead, according to one embodiment of the present disclosure.

FIG. 10 is a perspective view that schematically illustrates a sensor portion 360 of a lead 350 for an implantable stimulation system, according to one embodiment of the present disclosure. In one embodiment, the sensor portion 360 has at least substantially the same features and attributes as sensor portions 60, 260 as previously described herein. As illustrated in FIG. 10, sensor portion 360 is supported by a distal portion 356 of a lead body and at the other end, includes a distal tip 364. In one aspect, sensor portion 360 comprises a top portion 361 with its recessed portion 370 and a bottom portion 362.

In general terms, via recessed portion 370, sensor portion 360 provides a directional sensor lead with the recessed portion 370 defining the direction or orientation of sensing. With reference to the previously described wings 162 in FIG. 3 or wings 220 in FIG. 5, these wings act to keep recessed portion 370 in a desired orientation that faces the target tissue to be sensed.

In one embodiment, this recessed portion 370 defines a membrane portion 372 interposed between a pair of sloped walls 374 on opposite sides of the membrane portion 372. The membrane portion 372 forms part of a sensor element 400 contained within housing 412 of sensor portion 360.

Figure 11:
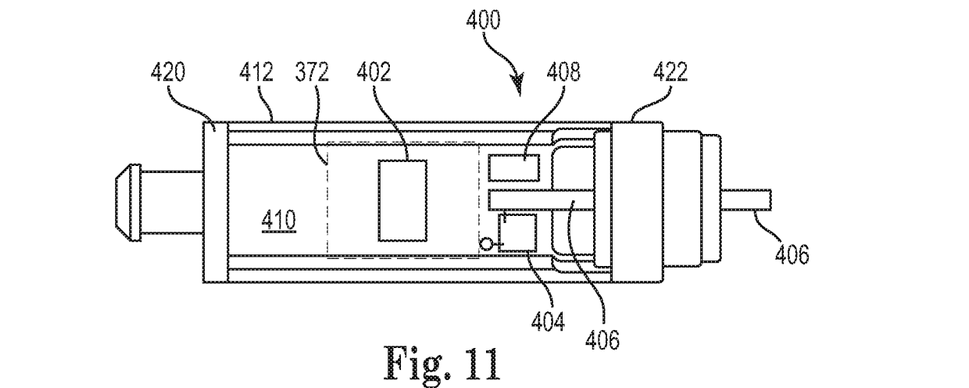
FIG. 11 is a sectional view as taken along lines 11-11 of FIG. 10, according to one embodiment of the present disclosure.
Figure 12:
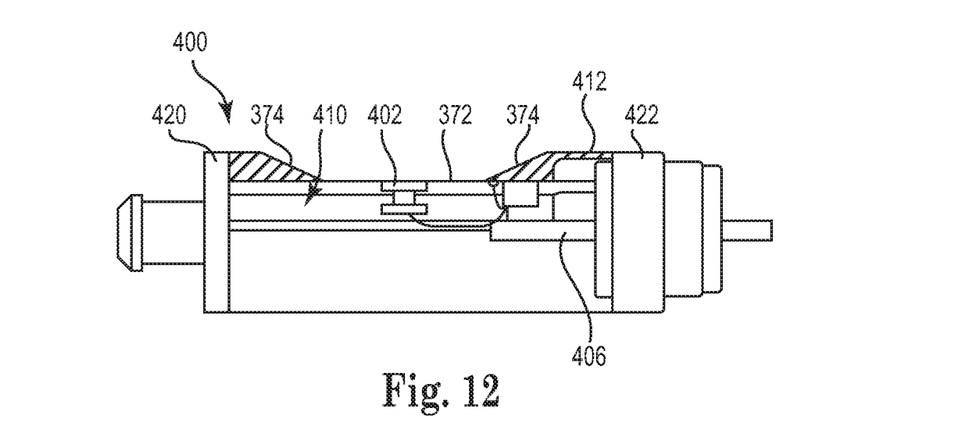
FIG. 12 is a sectional view as taken along lines 12-12 of FIG. 10, according to one embodiment of the present disclosure.

FIG. 11 is a sectional view as taken along lines 11-11 of FIG. 10, and FIG. 12 is side sectional view as taken along lines 12-12 of FIG. 10, both of which schematically illustrate sensor element 400, according to one embodiment of the present disclosure. In one aspect, this sectional view depicts membrane portion 372 in dashed lines. As illustrated in FIGS. 11-12, sensor element 400 comprises a housing 412 that contains a pressure sensing element 402 (e.g., pressure transducer) configured to measure sensed changes through or along membrane portion 372 and a temperature sensing element 404 (e.g., temperature transducer) configured to measure temperature. In one embodiment, the pressure sensing element 402 is electrically coupled to the temperature sensing element 404, which acts as a temperature compensation unit for pressure sensing element 402. In one aspect, the temperature sensing element 404 is positioned away from the membrane portion 372 and the pressure sensing element 402, so that these respective sensing elements 402, 402 are laterally spaced apart to each other, rather than in a stacked configuration.

In some embodiments, the temperature sensing element 404 is electrically coupled to the pressure sensing element 402 in order to cancel temperature effects and thereby produce a sensor element 400 that produces a sensed respiratory signal that primarily indicates changes in pressure and not temperature.

However, it is also understood that when pressure sensing element 402 comprises a piezo-electric element, pressure sensing element 402 is substantially more sensitive to changes in temperature than to changes in pressure. Accordingly, in some other embodiments, instead of attempting to cancel out temperature effects, the change in temperature sensed via the piezo-based pressure sensing element 402 is used as a factor in determining whether or not an obstructive sleep apnea event has occurred. As later illustrated in more detail in association with FIGS. 12-13 and 17, a temperature signal can be used, independent of or with a pressure signal, to identify an obstructive sleep apnea event.

Sensor element 400 also includes a transistor 408 to process or amplify the signals measured via the pressure sensing element 402 and the temperature sensing element 404. In some embodiments, the pressure sensing element 402 and/or the temperature sensing element 404 are piezoelectric transducers. In one aspect, the respective elements 402, 404 are in electrical communication with a conductive feed element 406 of sensor portion 260 of lead 250 that provides electrical connection out of the hermetically sealed housing 412. This feed element 406, in turn, communicates signals to IPG 55 (FIG. 1) to indicate a respiratory state or effort.

Figure 13:
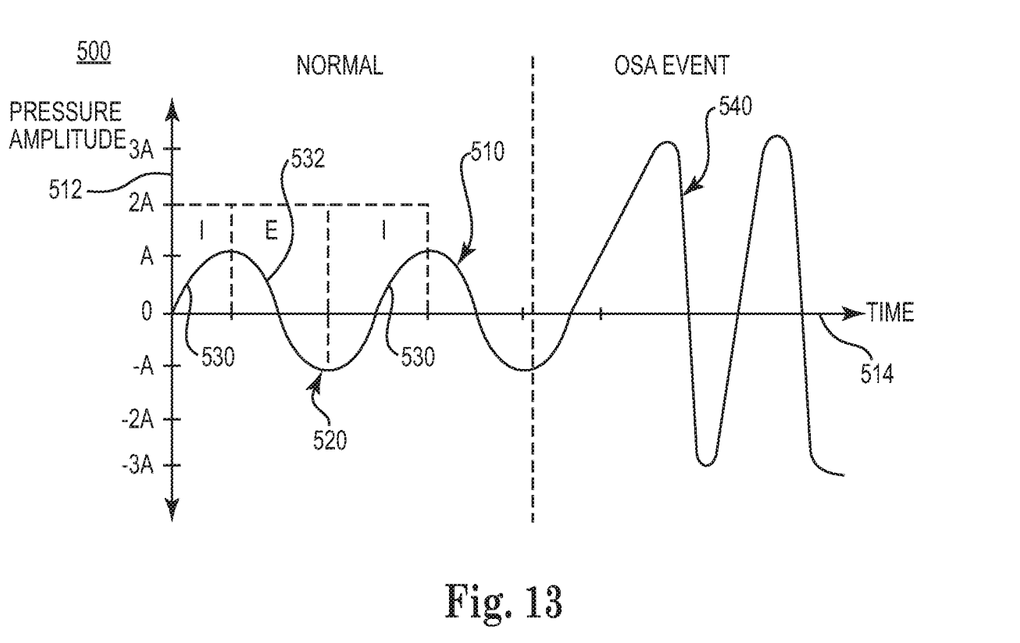
FIG. 13 is diagram schematically illustrating a respiratory pressure signal, according to one embodiment of the present disclosure.
Figure 14:
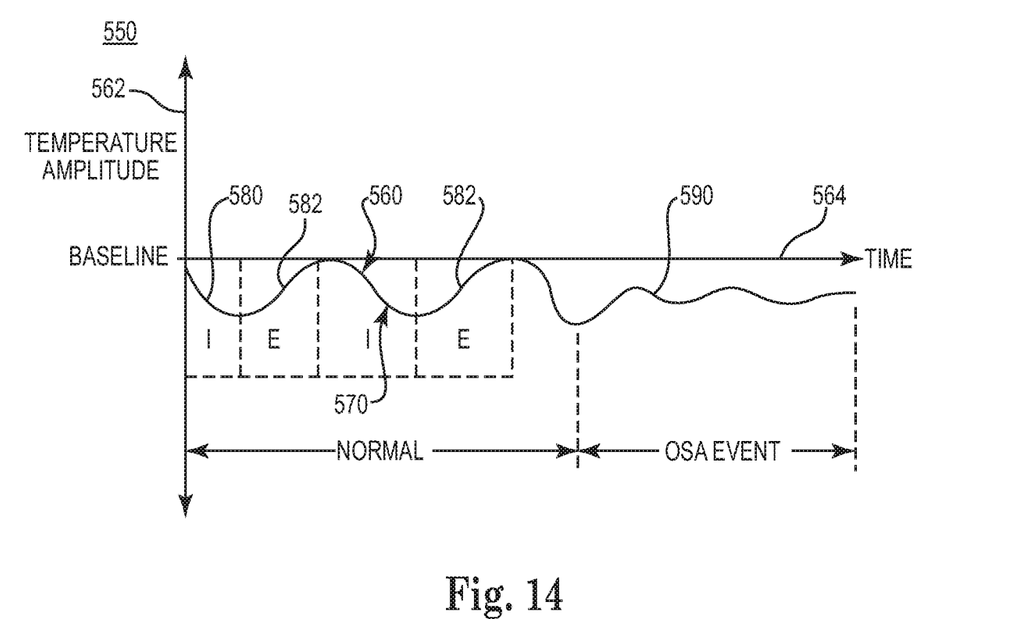
FIG. 14 is diagram schematically illustrating a respiratory-associated temperature signal, according to one embodiment of the present disclosure.

In some embodiments, the respiratory-associated signals produced from the pressure sensing element 402 and the temperature sensing element 404 are mapped independently, as illustrated in FIGS. 13-14. As illustrated in FIG. 13, a diagram 500 illustrates a signal 510 mapped as pressure (512) over time (514). Signal 510 includes cyclical patterns of inspiration (I) and expiration (E), with diagram 500 also illustrating the nature of these patterns during normal respiration (signal portion 520) and during an obstructive apnea (OSA) event (signal portion 540). During normal respiration, signal portion 520 includes inspiration portions 530 and expiration portions 532 which have a nominal amplitude (A) and which correspond to generally uniform cyclical amplitudes of respiratory pressure. However, during an OSA event, signal portion 540 reveals a substantially greater amplitude of respiratory pressure (such as, 3A or three times the nominal amplitude A in a non-limiting example), indicating increased respiratory efforts through the inspiratory and expiratory phases of the respiration cycle during an obstructive event. Accordingly, these dramatic changes in the cyclical amplitudes of the pressure signal are used to detect obstructive sleep apnea and/or to trigger stimulation therapy for treating the sleep apnea.

As illustrated in FIG. 14, a diagram 550 illustrates a signal 560 mapped as temperature (562) over time (564). Signal 560 includes cyclical patterns of inspiration (I) and expiration (E), with diagram 550 also illustrating the nature of these patterns during normal respiration (signal portion 570) and during an obstructive apnea (OSA) event (signal portion 590). During normal respiration, signal portion 570 includes inspiration portions 580 and expiration portions 582 which have a nominal amplitude (A), and which correspond to generally uniform cyclical amplitudes of the sensed temperature. However, during an OSA event, signal portion 590 reveals little difference between the peaks of the cyclical amplitudes of temperature between inspiration and expiration phases of the respiratory cycle, indicating a reduction of airflow. Accordingly, this lack of difference in the cyclical amplitudes of the temperature signal is used to detect obstructive sleep apnea and/or to trigger stimulation therapy for treating the sleep apnea.

Because such a temperature signal provides useful information regarding a state of respiration (normal vs. obstructive), one of the embodiments of the sensor element 400 described above used the temperature sensing element 404 independent of the pressure sensing element 404, i.e. not to compensate for temperature effects on the pressure signal. This temperature signal can stand alone or be combined with a pressure signal. Moreover, one of those embodiments, the piezo-electric sensing element 402 is used as a temperature sensor alone apart from pressure.

Figure 15:
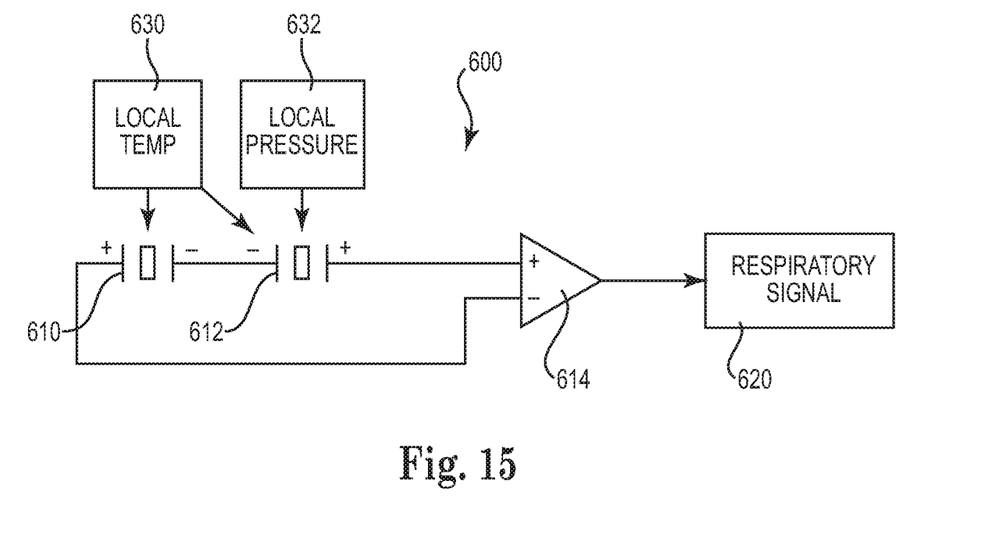
FIG. 15 is a diagram schematically illustrating a respiratory sensing circuit, according to one embodiment of the present disclosure.

FIG. 15 is diagram schematically representing an equivalent circuit 600 of the measurement of temperature and pressure via a sensor element, such as sensor element 400 of FIGS. 11-12, to produce a sensed respiratory signal 620. As illustrated in FIG. 15, circuit 600 includes a first piezo-electric element 610, a second piezo-electric element 612, and a transistor 614 (e.g., a transistor amplifier circuit). In one embodiment, a local tissue temperature 630 (where the sensor element 400 is implanted and oriented) is sensed via first piezo-electric element 610 and via second piezo-electric element 612. Likewise, a local tissue pressure 632 (where the sensor element 400 is implanted and oriented) is sensed via second piezo-electric element 612. In this arrangement, the pressure signal (captured via first sensing element 610) and the temperature signal (captured via second sensing element 612) are summed into one signal 620. In one embodiment, the first and second piezoelectric elements 610, 612 are electrically coupled together, to permit cancellation of the temperature effects on the sensing of pressure by the second piezoelectric element.

Figure 16:
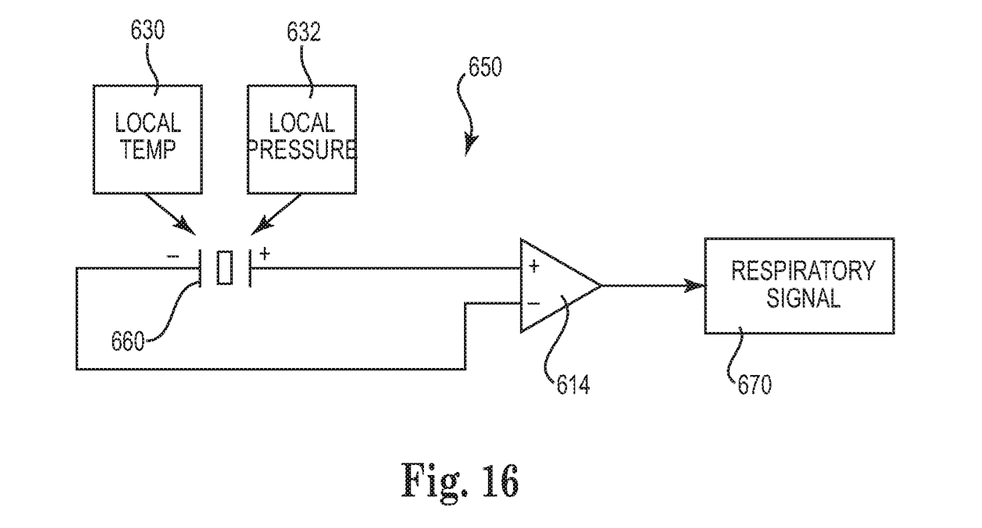
FIG. 16 is a diagram schematically illustrating a respiratory sensing circuit, according to another embodiment of the present disclosure.

In another embodiment, as illustrated schematically in FIG. 16, an equivalent circuit 650 for producing a sensed respiratory signal 670 includes just one piezo-electric element 660 and a transistor amplifier 614. In this embodiment, both a local tissue temperature 630 and a local pressure 632 (where the sensor element 400 is implanted and oriented) is sensed via the one piezo-electric element 660. It will be further understood that in some embodiments, various combinations of piezoelectric elements with different locations, different sizes, and/or different polarity connections could be created to scale the temperature and pressure responses.

In some other embodiments, the circuit 600 of FIG. 15 and the circuit of FIG. 16 are both implemented in a single sensor housing and, in this arrangement, both of the sensed pressure and sensed temperature signals would be sent separately from each other to the IPG 55.

In some embodiments, a temperature signal and a pressure signal could be provided as input to the pulse generator (e.g., IPG 55 in FIG. 1) as two separate signals to preserve maximum signal content.

Figure 17:
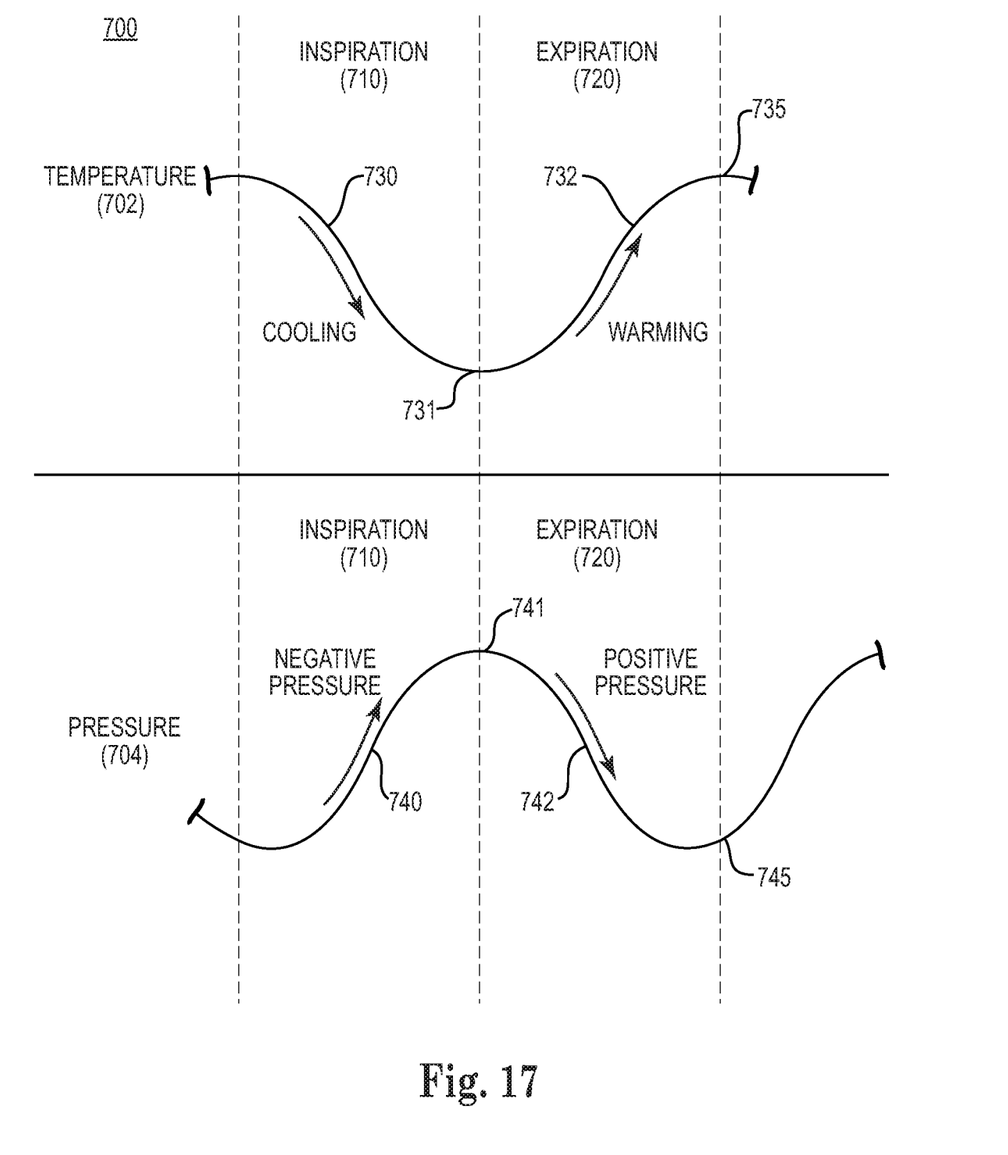
FIG. 17 is a diagram schematically illustrating both pressure and temperature components of a respiratory signal, according to one embodiment of the present disclosure.

FIG. 17 is a diagram 700 schematically illustrating a juxtaposition of an independent respiratory temperature signal 702 (through cycles of inspiration 710 and expiration 720) relative to a pressure signal 704 (through cycles of inspiration 710 and expiration 720). As shown in FIG. 17, during inspiration 710 the temperature falls in a cooling segment 730 (due to air temperature) and rises in a warming segment 732 (due to blood flow). Likewise, during inspiration 710, the pressure rises in a negative pressure segment 740 and falls during a positive pressure segment 742. As illustrated by FIG. 17, the lowest value 731 of the temperature signal 702 occurs simultaneously with a peak 741 of the pressure signal 704. In one aspect, in this embodiment, the piezo-electric element is mounted and connected with the appropriate polarities to cause the cooling temperature during inspiration and the negative pressure during inspiration to be additive. In this way, one can create an additive temperature and pressure signal.

In this way, the signals from both transducers, such as pressure and temperature, can be either utilized in combination, or utilized separately in a standalone configuration to determine whether therapy should be delivered. For example (of utilizing the signals separately) if the pressure is determined to increase beyond a predetermined pressure threshold while at the same time no changes in temperature are sensed due to restricted or obstructed airflow into the lungs, it is concluded that an obstruction has taken place, and therefore therapy is delivered or increased based on the sensed obstruction.

However, if the pressure is determined to increase beyond the predetermined pressure threshold while at the same time the temperature is also determined to increase beyond a predetermined temperature threshold (which indicates a deep breath rather than an obstruction), then therapy may be withheld. Alternatively, in this situation, further indicators such as input from an activity sensor, for example, may be required before delivery of therapy it is concluded that an obstruction has occurred and therapy is commenced.

In some embodiments, a sensed temperature signal is used to indicate a polarity of the sensed respiratory pressure and thereby differentiate inspiratory phases from expiratory phases of sensed respiratory pressure. In particular, as shown in FIG. 17, an inspiratory and expiratory pattern of the sensed temperature signal can be correlated with an inspiratory and expiratory pattern of the sensed respiratory signal. This arrangement is useful in certain instances in which the sensed respiratory pressure signal becomes inverted. In this situation, using the sensed temperature signal to differentiate the inspiratory and expiratory phases allows the IPG 55 to properly synchronize an application of electrical stimulation relative to the inspiratory phase, the expiratory phase, and/or a transition between the respective inspiratory and expiratory phases.

With reference to the sensed respiratory pressure signal shown in FIG. 17, it is further understood that peak 741 generally corresponds to a transition region (e.g. end of inspiration and/or onset of expiration) between the inspiratory phase (710) and the expiratory phase (720). Likewise, with further reference to the sensed temperature pressure signal shown in FIG. 17, it is understood that valley 731 generally corresponds to a transition region (e.g. end of inspiration and/or onset of expiration) between the inspiratory phase (710) and the expiratory phase (720). Moreover, it will be understood by those skilled in the art that such transition regions include information regarding the onset of inspiration, onset of expiration, and other related respiration timing fiducials. In one aspect, this information is used to trigger or synchronize the application of an electrical stimulation signal from IPG 55 to a stimulation lead (FIG. 1).

The pressure and temperature contribution to the sensor are provided above as illustrations of potential sources of input to the sensor signal. Other input is also possible, such as the local mechanical force associated with respiratory movement or other motion.

Embodiments of the present disclosure provide accurate sensing of respiratory effort suitable for detecting, and/or triggering therapy on, an obstructive sleep apnea event. With sensitivity to pressure and/or temperature, a sensing element provides robust capture of respiratory behavior to more accurately indicate the presence or absence of an obstructive sleep apnea event, thereby leading to a more efficacious delivery of therapy.

While at least one exemplary embodiment has been presented in the foregoing description, it should be appreciated that variations exist. It should also be appreciated that the exemplary embodiment or exemplary embodiments are only examples, and are not intended to limit the scope, applicability, or configuration of the present disclosure in any way. Rather, the foregoing description will provide those skilled in the art with a convenient road map for implementing the exemplary embodiment or exemplary embodiments. It should be understood that various changes can be made in the function and arrangement of elements without departing from the scope of the present disclosure.

What is claimed is:

1. A method of treating obstructive sleep apnea, the method comprising:
   locating and forming an extrapleural implant location within non-bony anatomy between a pair of immediately adjacent ribs on one side of a patient's body and lateral to a sternum of the patient's body;
   positioning a pressure-indicative sensor of a sensor lead in the extrapleural implant location in which the pressure-indicative sensor is coupled relative to a respiratory pressure of a pleural space without directly securing the pressure-indicative sensor at the location of the pressure-indicative sensor;
   inserting and advancing a distal portion of the sensor lead, including the pressure-indicative sensor, to orient the distal portion within the extrapleural implant location to be generally parallel to the adjacent ribs;
   providing the pressure-indicative sensor having a first side providing a single-direction sensing element and positioning the pressure-indicative sensor to cause the first side to directly face, and overlie, a portion of the lung on the one side of the patient's body;
   sensing, via the pressure-indicative sensor, the respiratory pressure; and
   triggering electrical stimulation of an airway-patency-related nerve, from an implantable pulse generator coupled to the sensor portion, based on at least one parameter of the sensed respiratory pressure.

2. The method of claim 1, wherein the one side of the patient's body is the right side, and comprising positioning the implantable pulse generator on the right side of the body.

3. The method of claim 1, wherein positioning the pressure-indicative sensor comprises:
   arranging the extrapleural implant location of the pressure-indicative sensor to be at or lateral to a costochondral joint of the adjacent ribs.

4. The method of claim 1, comprising: selecting the extrapleural implant location to be inferior to, and aligned with, a nipple on the one side of patient's body such that the alignment of the pressure-indicative sensor and the nipple is generally parallel to a longitudinal axis of the patient's body.

5. The method of claim 4, wherein locating and forming the extrapleural implant location comprises locating the implant location between the adjacent pair of ribs within a group of ribs extending from a second uppermost rib through a seventh uppermost rib.

6. The method of claim 5, wherein the adjacent pair of ribs comprises the fifth uppermost rib and the sixth uppermost rib.

7. The method of claim 1, wherein positioning the pressure-indicative sensor comprises:
   positioning and securing a fixed first anchor on the sensor lead in the extrapleural implant location; and
   securing, via the fixed first anchor, the pressure-indicative sensor relative to a subcutaneous tissue in the extrapleural implant location.

8. The method of claim 7, wherein the fixed first anchor is proximal to the pressure-indicative sensor.

9. The method of claim 8, comprising arranging the pressure-indicative sensor at a distal tip of the sensor lead.

10. The method of claim 7, wherein securing the pressure-indicative sensor comprises:
    providing the fixed first anchor as a pair of arms that extend generally perpendicular to, and outwardly from, opposite sides of a body of the sensor lead; and
    orienting the arms, in their secured position relative to the subcutaneous connective tissue between the adjacent ribs, in a direction generally perpendicular to the ribs to maintain a body of the pressure-indicative sensor to be generally parallel to the ribs and to maintain the first side of the pressure-indicative sensor to face toward the lungs of the patient's body.

11. The method of claim 10, comprising:
    securing, via a selectively movable second anchor on the sensor lead that is proximal to the fixed first anchor, the sensor lead relative to a tissue at a lateral side portion of a rib cage of the patient's body; and
    arranging a proximal portion of the sensor lead, proximal to the fixed first anchor, to extend along the lateral side portion of the rib cage of the patient's body, and generally parallel to a longitudinal axis of the patient's body, for connection to an implantable pulse generator.

12. The method of claim 7, wherein the fixed first anchor is spaced apart from the pressure-indicative sensor about 3 to 9 centimeters along a length of the sensor lead.

13. The method of claim 1, wherein locating and forming the extrapleural implant location comprises at least one of:
    locating the extrapleural implant location inferior to a pectoral muscle of the patient's body; or
    locating the intercostal, extrapleural implant location between a second uppermost rib and a sixth uppermost rib, of the patient's body.

14. The method of claim 1, wherein the extrapleural location comprises an intercostal location.

* * * * *